United States Patent [19]

Ellis et al.

[11] 4,227,151
[45] Oct. 7, 1980

[54] MEASUREMENT AND MONITORING OF THE ELECTRICAL CONDUCTIVITY OF LIQUOR SAMPLES

[75] Inventors: Christopher I. A. Ellis; Edward L. Naylor, both of Birkenhead, England

[73] Assignee: Malcom-Ellis (Liverpool) Limited, Liverpool, England

[21] Appl. No.: 937,175

[22] Filed: Aug. 28, 1978

[30] Foreign Application Priority Data

Aug. 27, 1977 [GB] United Kingdom ............... 36088/77

[51] Int. Cl.² .......................................... G01N 27/42
[52] U.S. Cl. .................................... 324/448; 324/441
[58] Field of Search ................. 324/29, 158 P, 30 R, 324/30 B, 448, 441; 204/1 T

[56] References Cited

U.S. PATENT DOCUMENTS 3,115,602 12/1963 Sutton et al. ...................... 324/30 B
3,701,006 10/1972 Volkel ............................... 324/30 B

Primary Examiner—Michael J. Tokar
Attorney, Agent, or Firm—Kenyon & Kenyon

[57] ABSTRACT

A measuring cell for use in measuring and monitoring the electrical conductivity of a liquid. The cell comprises at least four concentric circular electrodes which are disposed in a flat or substantially flat surface. The concentric electrodes are mutually separated by annular areas of electrically non-conductive material.

Also disclosed are a system for monitoring the electrical conductivity of a liquor sample and a system for comparing the electrical conductivities of two liquor samples both of which systems include a measuring cell having the aforegoing construction.

10 Claims, 6 Drawing Figures

MEASUREMENT AND MONITORING OF THE ELECTRICAL CONDUCTIVITY OF LIQUOR SAMPLES

The present invention relates to the measurement and monitoring of the electrical conductivity of liquor samples, such as laundry wash and rinse liquors.

It is known to continuously sample the conductivity and hence the electrolytic content of a laundry wash liquor in order to use the information derived from the state of the liquor to formulate and control the wash and rinse programmes, the conductivity depending inter alia upon the quantities of alkali and other cleansing agents added during the wash cycle(s) and removed during the rinsing cycle(s).

It is known to position a cell having at least four electrodes in the washing vessel so that the electrodes are in intimate contact with the wash or rinse liquor being sampled. The electrical conductivity is measured using such a four electrode cell by connecting the outer pair of electrodes to an alternating current source, the magnitude of the voltage across the inner pair of electrodes being monitored and being kept substantially constant by way of a closed a.c. feedback loop which varies the magnitude of the alternating current. The value of the alternating current is thus dependent upon the conductivity of the liquor sample and may be directly measured or compared with a reference signal.

The electrical conductivity of a liquor sample may also be measured using cells having more than four electrodes. In the latter instance four of the electrodes are connected as described above and the additional electrodes are used to ensure that the operation of the cell is predictable, for example, by setting up clearly defined electron paths within the liquor in the cell.

The closed a.c. feedback loop used previously must have a high internal gain if the system is to be capable of a wide range of measurement. One problem with the known a.c. feedback loop referred to above is that, because this has used series amplifier circuits which inevitably have internal phase shifts, the maximum gain which can be achieved, while maintaining stability of the loop, has been limited. Care has also had to be taken in the physical layout of the amplifier circuits to minimize stray wiring reactances which can also cause instability.

The known multi-electrode conductivity cells referred to above have been of cylindrical construction, with spaced, linearly aligned annular or cylindrical electrodes so arranged as to form part of the inner wall of a cylindrical or tubular container. The underlying reasons for adopting the latter form of construction were principally to enable the measuring cell to be incorporated in a flow line system and to permit the incorporation of guard electrodes to define the electric field within the cell. The inclusion of field defining electrodes within the cylindrical construction also made possible modifications to the basic structure to produce a measuring cell which could be inserted into a vessel or machine instead of being part of a flow line system (see for example our GB Pat. No. 1460892).

However, cylindrical or tubular type conductivity cells have numerous disadvantages, including the following:

(a) they are very costly to produce, needing as they do the use of special jigs and tools and requiring a multiplicity of sequential manufacturing processes;

(b) it is difficult to ensure consistency of performance in production since the relative spacing of the electrodes is critical;

(c) in the case of insertion cells which are to be inserted into other machines, problems in siting arise due to the physical shape and dimensions of the cell unit;

(d) when insertion cells are used in, for example, industrial washing machines, problems arise due to the entry of foreign bodies, such as buttons, pins and assorted debris, which may necessitate the removal of the cell from the machine in order to dispose of them.

It is a principal object of the present invention to provide a conductivity cell in which the aforegoing disadvantages of the known cells are reduced.

In accordance with one aspect of the present invention, there is provided a measuring cell for use in measuring and monitoring the electrical conductivity of a liquid, comprising at least four concentric, circular electrodes disposed in or on a surface and mutually separated by annular areas of electrically non-conductive material.

Preferably, said surface is flat and is supported by a main body portion of the cell, the body portion being adapted to be mounted in a vessel or machine so as to present said surface, and hence the concentric electrodes, to a liquid under test.

Advantageously, the body portion is adapted to be inserted into a suitable aperture in the wall of a vessel or machine containing the liquid under test, the arrangement being such that said surface carrying the electrodes then lies flush with the internal wall surface of said vessel or machine.

In one embodiment, the body portion is tubular and defines the outer one of said concentric electrodes, the inner electrodes being respectively defined by one end of each of a plurality of cylindrical metallic members coaxially disposed within the tubular body portion and mutually spaced apart by tubular spacers of electrically non-conductive material.

In other embodiments, the body portion is tubular but does not itself form an electrode, the electrodes being respectively defined by one end of each of a plurality of cylindrical metallic members coaxially disposed within the tubular body portion and mutually spaced apart by tubular spacers of electrically non-conductive material.

Conveniently, the central, inner electrode can be hollow to receive a temperature sensitive element, such as a thermistor.

In accordance with a second aspect of the present invention there is provided a system for monitoring the electrical conductivity of a liquor sample, comprising a measuring cell having at least four concentric, circular electrodes disposed in or on a surface and mutually separated by annular areas of electrically non-conductive material, said surface being presented, in use of the system, to said liquor sample under test, a high impedance alternating current source connected across a first pair of said electrodes, means for producing a direct current signal which is dependent upon the alternating voltage across a second pair of said electrodes comprised by electrodes intermediate said first pair, means for deriving a control signal from said direct current signal and applying the control signal to said high impedance alternating current source to vary the current applied to said first pair of electrodes in dependence upon the conductivity of the liquor sample, and means for measuring said current applied to the first pair of electrodes to derive a signal dependent upon the conductivity of the liquor sample.

In a preferred embodiment of the invention said means for producing the direct current signal comprises a high input impedance amplifier connected across the second pair of electrodes, the output from said amplifier being fed to a rectifier to produce the direct current signal, and the rectifier being constructed such that the direct current signal is proportional to the peak value of the alternating voltage. The output of the rectifier may be connected to a low pass filter. Preferably said means for deriving and applying the control signal comprises a voltage controlled attenuator connected to the output of the rectifier or filter. The attenuator is connected to an alternating current source to produce an alternating current output which is substantially inversely proportional to said direct current signal and which forms said control signal.

The measuring cell preferably includes four electrodes but more than four can be incorporated as required. In certain instances, circuit requirements may necessitate the fourth electrode to be floating, i.e. not connected to earth and in this case a fifth electrode concentric with the other electrodes may be added to function as an earth shield which in some instances may be the body of the cell. One or more of the cables attached to the electrodes may be shielded.

In accordance with a further aspect of the present invention there is provided a method of measuring the electrical conductivity of a liquor sample comprising presenting the liquor to an electrode cell having at least four concentric, circular electrodes disposed in or on a surface and mutually separated by annular areas of electrically non-conductive material, passing an alternating current from a high impedance source through a first pair of said electrodes, producing a direct current signal dependent upon the alternating voltage across a second pair of said electrodes comprised by electrodes intermediate said first pair, deriving a control signal from said direct current signal and applying the control signal to said high impedance alternating current source to vary the current applied to said first pair of electrodes such as to maintain said alternating voltage constant. The value of the current may then be either directly measured or compared with a reference signal. The reference signal may be derived from a reference source or from a reference cell.

The references to a high impedance alternating current source in the specification refer to a current source of sufficiently high impedance to ensure that the magnitude of the current flowing in the cell is sensibly independent of the overall resistance in the cell.

In accordance with yet a further aspect of the present invention there is provided a system for comparing the electrical conductivities of two liquor samples, comprising a pair of electrode cells, one for presentation to each of the two liquor samples, respectively, each cell having at least four concentric, circular electrodes disposed in or on a surface and mutually separated by areas of electrically non-conductive material, said surfaces being presented, in use of the system, to said two liquor samples, respectively, a pair of high impedance alternating current sources respectively connected across a first pair of the electrodes of the cells, means for producing respective direct current signals which are dependent upon the alternating voltages across second pairs of said electrodes comprised by electrodes intermediate said first pairs, means for deriving a control signal from the direct current signal from one of said cells and applying this control signal to both the high impedance alternating current sources to vary the current applied to both said first pairs of electrodes in dependence upon the conductivity of the liquor sample in contact with said one of the cells, and means for comparing the two direct current signals from the second pairs of electrodes to provide a signal which depends upon the conductivities of the two liquor samples.

The invention is described further hereinafter, by way of example, with reference to the accompanying drawings, in which.

Figure 1:
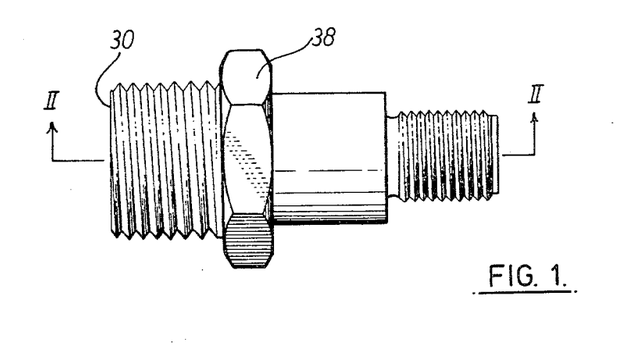
FIG. 1 is a side or plan view of one embodiment of a conductivity measuring cell in accordance with the present invention.
Figure 2:
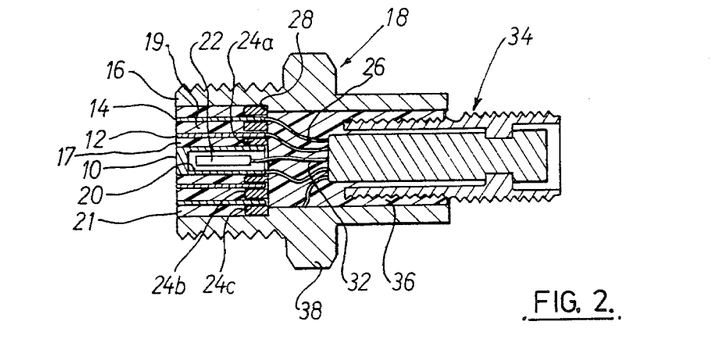
FIG. 2 is a section on II—II in FIG. 1.
Figure 3:
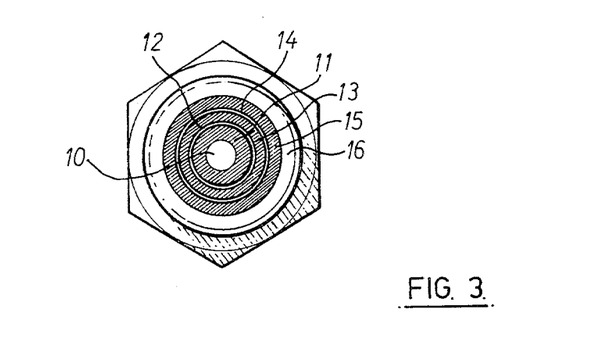
FIG. 3 is a front view of the measuring cell of FIG. 1.

The measuring cell of FIGS. 1 to 3 comprises four coaxially disposed cylindrical electrode forming members 10, 12, 14 and 16, preferably of stainless steel. The outer electrode 16 is, in this embodiment, formed by the outer body 18 of the measuring cell and has an external screw thread by which the cell can be inserted into its operational position in an internally screwthreaded bore in a vessel or machine (not shown). The inner electrode 10 is formed by a stainless steel rod which can optionally have a central bore 20 for receiving a temperature sensitive device 22, such as a thermistor. The intermediate electrodes 12, 14 which are the "voltage electrodes" of the device, comprise lengths of thin-walled stainless steel tube.

The inner electrodes 10, 12, and 14 are positively located relative to one another by means of coaxial, electrically non-conductive spacer bushes 24a, 24b, 24c, for example of nylon, which remain as a permanent feature of the device. Prior to assembly, each electrode 10 to 16 has a stainless steel lead-out wire 26 welded to it. During assembly, the bushes 24 with the electrodes 10, 12 and 14 therebetween are inserted into the left hand end of the outer body 18 (as viewed in FIG. 2) until the outer bush 24c engages an inwardly directed shoulder 28 on the outer body, the lengths of the electrodes 10, 12 and 14 being such that their outer ends then lie substantially in line with the left hand end of the body 18. The three annular spaces between the electrodes 10, 12, 14 and 16 are then filled up with a chemical resistant resin, such as Araldite, and the whole assembly is heat treated to cure the resin. The resin between the electrodes 10, 12, 14 and 16 thus effectively forms three cylindrical spacers 17, 19 and 21. When the resin is completely cured, the left hand end of the assembly is ground down so as to provide a flat circular end surface 30 containing concentric end faces of the four electrodes mutually separated by areas 11, 13 and 15 of resin filler.

In this embodiment, the lead-out wires 26 from the electrodes 10 to 16 and lead-out wires 32 from the thermistor 22 are connected to a conventional plug or socket connector 34 mounted in the right hand end of the body 18. The connector 34 is preferably mounted in the body 18 by means of a further mass 36 of resin which electrically and thermally isolates the connector 34 from the body 18 and also rigidly holds the connecting wires 26 and 32 in place.

The body 18 has an external nut 38 integrally formed thereon to enable the body to be screwed into its operational position.

The external electric field of the aforegoing cell is found to extend less than one radius into the mass of electrolyte being examined and readings given thereby are therefore sensibly independent both of the volume of electrolyte involved and the presence of nearby metallic or conductive material.

In addition to the aforegoing, this cell has the following practical advantages compared with the known "flow through" type discussed initially.

(i) it is inexpensive to produce, needing no special moulds, jigs or special assembly tools;
(ii) it is easily reproduceable and therefore needs no individual calibration processes;
(iii) it is of relatively small dimensions, thus easing installation and siting problems;
(iv) it is of inherently rugged construction so substantially eliminating the possibility of damage in use;
(v) the limited external electric field associated with this device enables the need for guard rings or electrodes to be dispensed with in some instances;
(vi) in its operational position, the face 30 of the device containing the effective parts of the electrodes can be arranged to be coplanar (i.e. flush) with the adjacent internal surface of the vessel or machine into which the cell is inserted so that there are no holes or cavities in which debris might collect;
(vii) the device provides convenient location for suitable temperature sensitive elements used for measurement control and compensation purposes.

In other embodiments, the outer body 18 and/or the electrodes 10 to 14 could be of metals other than stainless steel although the latter is preferred due to its ruggedness and freedom from chemical attack. The positions where the lead-out wires are attached to the electrodes need not be as shown in FIG. 2 but could be to the left of the bushes 24 as viewed in this Figure. The central electrode 10 need not contain the bore for the temperature sensitive device if the latter is not required.

Further electrodes in addition to those illustrated may be used in which case they would be mounted similarly to the electrodes of the illustrated embodiment. For example, the outer electrode need not be formed by the body 18 but could be a further electrode similar to the intermediate electrodes 12, 14. The connector 34 need not be incorporated in the body 18 but could be at a distant location or be dispensed with altogether, the wires 26, 32 emerging directly from the mass of resin 36 into a connecting cable (not shown).

Figure 4:
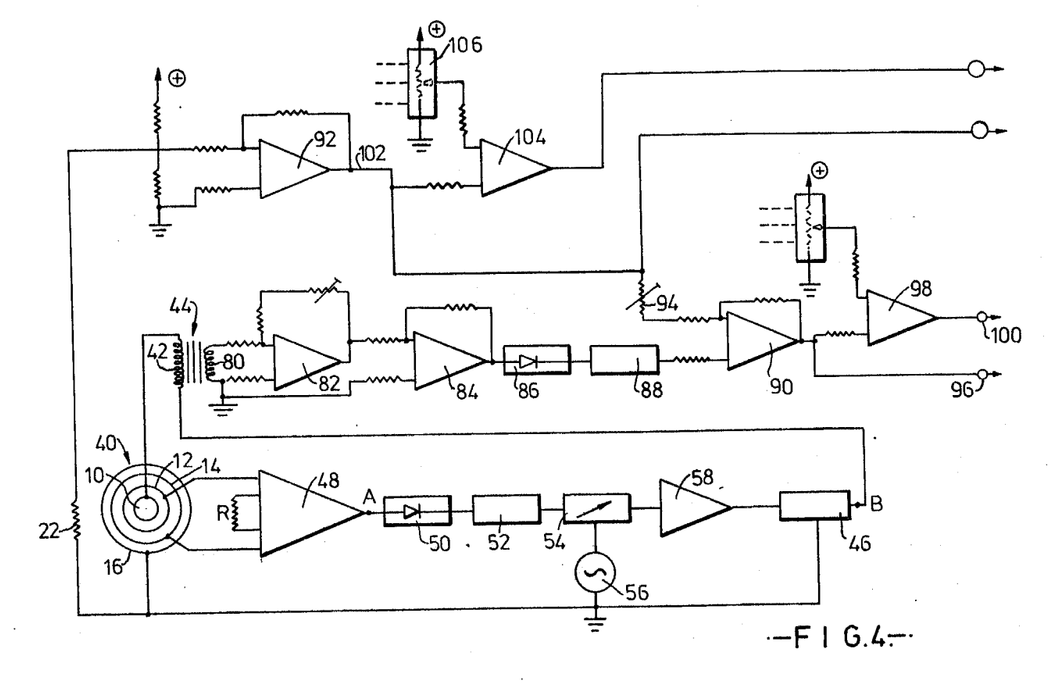
FIG. 4 is a schematic circuit diagram of one embodiment of a conductivity measuring apparatus in accordance with the invention.

FIG. 4 illustrates a system for producing an electrical output which is directly proportional to the conductivity of a liquor sample under test, this system incorporating a cell of the type illustrated in FIGS. 1 to 3 and a feedback loop of the type described and claimed in our copending British Application No. 9086/75.

The cell is indicated at 40 in FIG. 4, its outer electrode 16 being connected to earth and its inner electrode 10 being connected via the primary winding 42 of a current transformer 44, to the output of a high impedance alternating current source 46 which serves to pass an alternating current through the liquor sample with which the cell 40 is arranged to be in contact. Conveniently, the frequency of the current source 46 is 1KHZ.

The intermediate electrodes 12, 14 are connected to the input of a high input impedance amplifier 48 which monitors the voltage across the latter electrodes. The current source 46 is arranged to cause a current to flow through the liquor sample which is sensibly independent of the overall resistance of the cell. The amplifier 48 monitors the potential drop across the liquor sample between the two intermediate electrodes 12, 14. This potential drop is an inverse function of the conductivity of the liquor sample. In view of the high input impedance of the amplifier 48, the inner electrodes 12, 14 carry only a very small current and therefore the potential drop across the electrodes 12, 14 is substantially independent of any fouling of these electrodes.

Fouling of the outer electrodes 10, 16, however, causes the voltage across them to rise. This increase in voltage may be used to indicate the state of fouling of the outer electrodes 10, 16, for example by connecting an alarm (not shown) across the outer electrodes 10, 16 which operates when the voltage rises to a predetermined value. When the cell is used to measure the alkalinity of the liquor in a laundry washing machine, for example, the increase in voltage may be used to operate a voltage level device to trigger a visible or audible alarm and/or to shut down the laundry machine.

As is shown in FIG. 4, the output of the high input impedance amplifier 48 is connected to a precision rectifier circuit 50, of a type referred to hereinafter as a "zero level rectifier", whose output is in turn connected to a low pass filter 52. The output of the filter 52 is connected to a voltage controlled attenuator 54 to which an alternating current source 56 is also connected. The output of the voltage controlled attenuator 54 is fed to an amplifier 58 which is connected to a control input of the alternating current source 46. The circuit components connected between points A and B marked in FIG. 4 are shown in more detail in FIG. 6.

Figure 6:
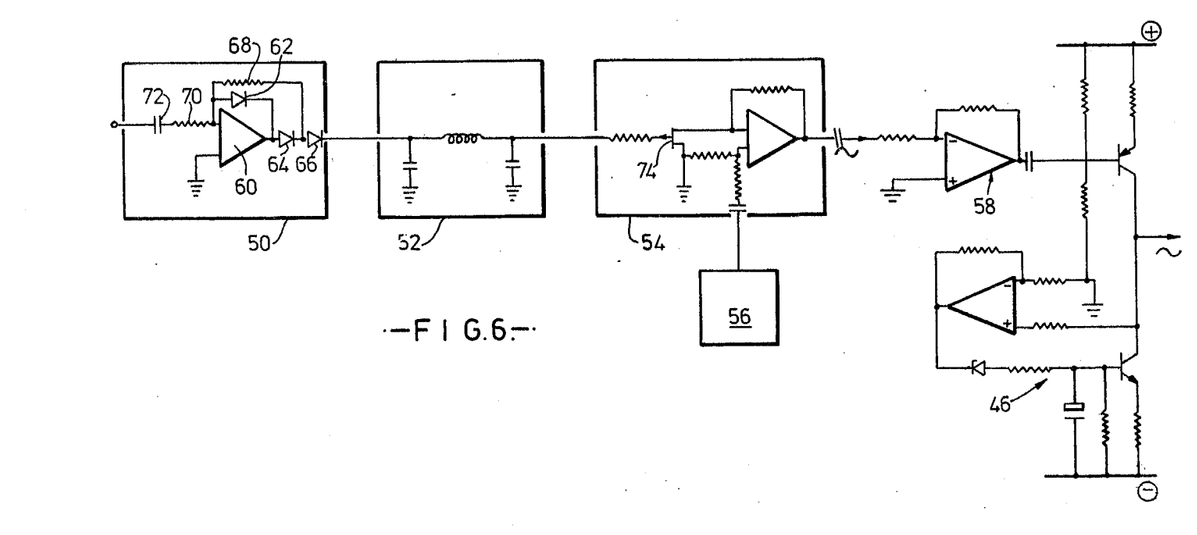
FIG. 6 is a circuit diagram illustrating a common part of the circuits of FIGS. 4 and 5 in more detail.

The a.c. voltage across inner electrodes 12, 14 is monitored by the high input impedance amplifier 48 and is fed to the zero level rectifier 50. As shown in FIG. 6, the zero level rectifier 50 comprises an operational or other high gain amplifier 60 having a first diode 62 connected between its output and its inverting input. Its non-inverting input is earthed. The output of the amplifier 60 is connected to the next stage, i.e. the filter 52, via the series combination of second and third diodes 64 and 66, all three diodes being orientated in the same conductive direction. A resistor 68 is connected between the inverting input of the amplifier 60 and the junction of the diodes 64 and 66 and serves, in co-operation with an input resistor 70 to set the gain of the amplifier 60. A capacitor 72 is connected in front of the resistor 70 to isolate the amplifier input from extraneous d.c. levels.

The operation of the zero level detector 50 is such that its d.c. output is directly proportional to the peak value of the a.c. voltage from the amplifier 48. If a simple diode were used on its own, the non-linear part of its characteristic at low input voltages would result in the desired direct proportionality being lost. The circuit 50 overcomes this in that the amplifier 60 acts to switch the diode 62 hard on or hard off immediately the input voltage departs from zero in one or the other direction respectively whereby the linear part of the diode characteristic is utilised at all times.

The low pass filter 52 removes any a.c. components from the output of the rectifier 50. The d.c. output from the low pass filter 52 is then applied to the gate of a field effect transistor 74 which acts as the voltage sensitive input of the voltage controlled attenuator 54. The voltage controlled attenuator 54 controls the amplitude of the alternating current source 56 so that the amplitude of the a.c. output of the attenuator 54 is inversely proportional to the d.c. output of the rectifier 50. The a.c. output of the attenuator 54 is fed by way of the high gain amplifier 58 to the alternating current source 46 to control the output thereof, the current source 46 being constructed to have an extremely high output impedance so as to ensure that the magnitude of the current supplied thereby is substantially independent of the overall resistivity of the cell circuit and is therefore not affected by fouling or contamination of the surfaces of the current electrodes 10, 16. The aforegoing components define a feedback circuit which is arranged to act to maintain the voltage across the intermediate electrodes 12, 14 substantially constant whatever the conductivity of the liquor in contact with the cell, the output of the current source 46 being varied to achieve this. Thus, in use, alternating current from the source 56 (typically 1 KHZ) is applied to the voltage controlled attenuator 54 and thence via the interface amplifier 58 to the high output impedance current generator 46, through the primary winding of the current transformer 44 to the central electrode 10 of the measuring cell, and back to the source 56 via the outer electrode 16 of the cell. The voltage produced by the latter current across the intermediate voltage electrodes 12, 14 is applied to the input of the high input impedance differential instrumentation amplifier 48 which is of high gain. The output of the amplifier is applied to the precision rectifier 50 which produces a d.c. output voltage directly proportional to the peak a.c. output of amplifier 48. After smoothing by the low pass filter 52, the d.c. output voltage of the rectifier is applied to the input of the voltage controlled attenuator such that the a.c. output of the attenuator is inversely proportional to the d.c. input control voltage. In this manner, the current through the cell is varied to maintain the a.c. voltage at the voltage electrodes 12, 14 constant irrespective of the conductivity of the liquor in contact with the cell. The magnitude of the current applied to the outer electrodes 10, 16 is thus proportional to the conductivity of the liquor in contact with the cell. The special design of this feed back circuit enables high internal gains to be achieved without any of the usual problems of instability and spurious oscillation.

To enable a direct measurment of the conductivity of the liquor in contact with the cell 40 to be made and/or to provide a control signal for controlling the conductivity value of the liquor, for example in a laundry washing machine, the magnitude of the current applied to the outer electrodes 10, 16 by the constant current generator is measured utilising the current transformer 44. The output voltage produced in the secondary winding 80 of the current transformer 44 is amplified in amplifiers 82 and 84, rectified in a precision rectifier 86, constructed similarly to the precision rectifier 50, smoothed in a low pass filter 88 and applied to one input of a differential amplifier 90. The other input at the amplifier 90 is supplied with a temperature compensating signal derived from the thermistor 22 located within the inner current electrode 10 of the cell 44, the temperature compensating signal being derived from the thermistor 22 via a d.c. amplifier 92 and an adjusting potentiometer 94. The resultant output signal at the amplifier 90 provides a temperature compensated signal which is directly related to the conductivity of the liquor. This signal can be picked off at an output terminal 96. The latter signal is also applied to one input of a comparator 98 where it is compared with an adjustable, preset reference voltage to produce at a second output terminal 100 a control signal which may be used to automatically control the addition of supplies of suitable chemicals to the liquor to maintain a desired level of conductivity.

The output of the temperature compensating circuit appearing on the line 102 may also be used to control a source of heat (not shown), via a comparator 104 and an adjustable pre-set reference voltage from a temperature reference 106, to maintain a desired temperature level for the liquor.

Figure 5:
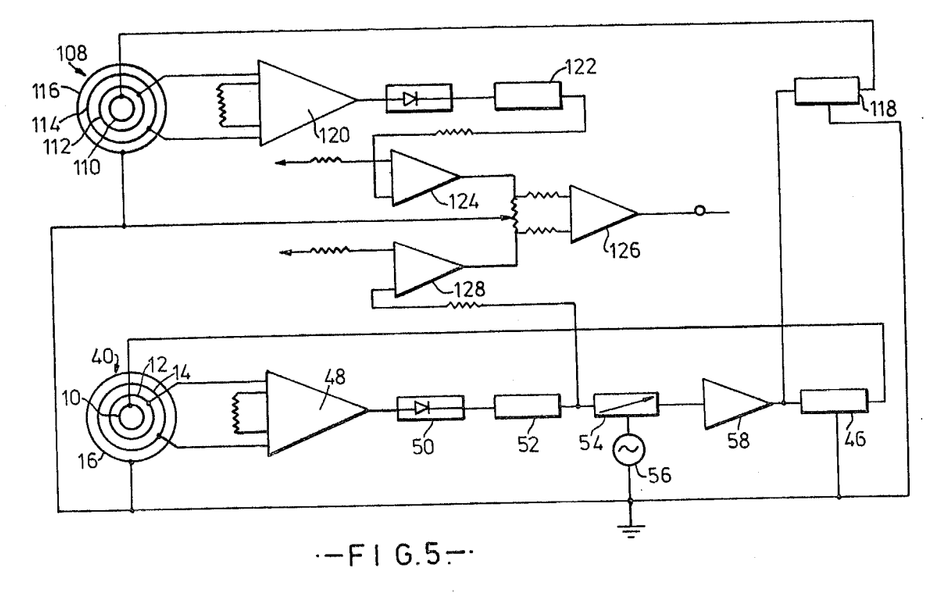
FIG. 5 is a schematic circuit diagram of one embodiment of a conductivity comparison apparatus in accordance with the invention.

It is often required that the electrical conductivity of a liquor should be compared with that of a reference liquor in a further reference cell to provide a signal for controlling the addition of chemicals or a dilutant. FIG. 5 schematically illustrates such an arrangement. In FIG. 5, parts common to FIG. 4 have been given the same reference numerals. One situation in which such a comparison can be helpful is where, during a washing and rinsing process, it is necessary to compare the electrolytic content of the mains water supply with that of the sample being monitored within the washing vessel. More particularly, during the rinsing cycle, it is usually required that the content of dissolved solids and electrolyte be reduced to result in a conductivity level which has a predetermined relationship with the conductivity and hence the electrolytic content of the incoming mains water. The reason for this is that the electrolytic content of the mains water varies considerably over short durations of time and in different locations and it is therefore only by utilising the readings obtained from two cells, one in the incoming mains water supply and the other in the rinsing vessel, that it is possible to take account of such variations. If one did not take such variations into account but merely sought to reduce the absolute value of the conductivity of the rinse liquor to a predetermined value irrespective of the prevailing conductivity of the incoming mains water, then, depending upon the value of the latter conductivity, it may become impossible to reach the predetermined value no matter how much mains water is added and hence unnecessary time and expense will be incurred.

In FIG. 5, the basic loop circuit is exactly the same as in FIG. 4 but with the exclusion of the current transformer 44 which is not required. The second, reference cell 108 is constructed identically to the cell 40 and has current electrodes 110, 116 and voltage electrodes 112, 114. A second high impedance current generator 118, identical to the generator 46, is driven in an identical fashion to the generator 46 by the output of the interface amplifier 58 whereby a current of identical magnitude to that in the measuring cell 40 is passed through the reference cell 108. The voltage across the intermediate electrodes 112, 114 of the reference cell is applied to a high input impedance, high gain amplifier 120 whose output is rectified in a further precision rectifier, corresponding in construction to the rectifier 50, smoothed in a low-pass filter 122 and applied to one input of a comparator 124. The other input of the comparator 124 is supplied with a temperature compensating signal, the temperature compensated output being in turn applied to one input of a further comparator 126. The other input of the comparator 126 is obtained from the output of a comparator 128 whose inputs respectively receive the output of the low-pass filter 52 in the main feedback loop and a temperature compensating signal.

Due to the feedback action of the measuring cell loop circuit, the voltage at the output of the low-pass filter 52 will remain sensibly constant, this voltage being applied, after temperature compensation, to the one input of the comparator 126. The output from the reference cell, taken from across its voltage electrodes 112, 114 and rectified and filtered, is dependent upon two principal factors, namely (1) the conductivity of the reference cell liquid and (2) the current passed through the reference cell by generator 118 which is identical to that through the measuring cell 40 and which is in turn dependent on the conductivity of the liquor in contact with the measuring cell, as explained above. By comparing the outputs of the two circuits in the comparator 126, a complex signal is obtained which involves the conductivities of the two liquids under comparison and which achieves a predetermined value only when the conductivities of the two samples are the same.

Thus, in the example mentioned above when it is desired to dilute the liquor sample during rinsing until its conductivity is reduced to be substantially equal to that of the incoming mains supply, dilutant is added to the rinse water until the output of the comparator 126 arrives at said predetermined value indicative of identity of conductivity. Attempts to further dilute the rinse liquid are then arranged to be inhibited since of course no such further dilution can occur and attempts to do so would only waste water and time. Obviously, however, to rinse to complete equality of the conductivities of the rinse liquid and the incoming water supply would require an infinite number of rinse liquid changes in the rinsing vessel and so, in practice, a small offset adjustment is provided at the comparator 126 whereby complete identity of the conductivities is not quite required in order to achieve said predetermined output signal level. By this means, it has been found that an almost constant small difference between the conductivities of the incoming water and the final rinse liquor can be maintained, irrespective of random variations in the conductivity of the incoming mains water.

Temperature compensation as described above is necessary due to the fact that the temperatures of the two liquors under comparison are not necessarily the same.

Whereas FIGS. 4 and 5 show separate arrangements for direct measurement and comparison tests, respectively, they could alternatively be combined into a single system with suitable switching to select the desired operation of direct measurement or comparison. This could be achieved substantially along the lines of FIG. 3 of our aforementioned copending British Application No. 9086/75.

Whereas the use of the invention has been described in conjunction with a laundry washing and rinsing system, the invention can equally be used for the measurement and/or control of (electrolytic) solutions in other situations.

Whereas in the described embodiment the cell is adapted to be screwed into its operational position, other means of mounting and inserting the cell may be used where more convenient.

We claim:

1. A measuring cell for use in measuring and monitoring the electrical conductivity of a liquid, comprising at least four concentric circular electrodes disposed in a surface and mutually separated by annular areas of electrically non-conductive material, said surface being flat and being supported by a main body portion of the cell, the body portion being adapted to be mounted in a vessel or machine for presenting said surface, and hence the concentric electrodes, to a liquid under test, the body portion being tubular and defining the outer one of said concentric electrodes, the inner electrodes being respectively defined by one end of each of a plurality of cylindrical metallic members coaxially disposed within the tubular body portion and mutually spaced apart by tubular spacers of electrically non-conductive material, and the central, inner electrode being hollow to receive a temperature sensitive element.

2. A measuring cell for use in measuring and monitoring the electrical conductivity of a liquid, comprising at least four concentric circular electrodes disposed in a surface and mutually separated by annular areas of electrically non-conductive material, said surface being flat and being supported by a main body portion of the cell, the body portion being adapted to be mounted in a vessel or machine for presenting said surface, and hence the concentric electrodes, to a liquid under test, the body portion being tubular but not itself forming an electrode, the electrodes being respectively defined by one end of each of a plurality of cylindrical metallic members coaxially disposed within the tubular body portion and mutually spaced apart by tubular spacers of electrically non-conductive material, and the central, inner electrode being hollow to receive a temperature sensitive element.

3. A measuring cell according to claims 1 or 2 in which the body portion is adapted to be inserted into a suitable aperture in the wall of a vessel containing the liquid under test, whereby said surface carrying the electrodes can then lie flush with the internal wall surface of said vessel.

4. A system for monitoring the electrical conductivity of a liquor sample, comprising a measuring cell having at least four concentric, circular electrodes disposed in a flat surface and mutually separated by annular areas of electrically non-conductive material, said surface being presented, in use of the system, to said liquor sample under test, a high impedance alternating current source connected across a first pair of said electrodes, means for producing a direct current signal which is dependent upon the alternating voltage across a second pair of said electrodes comprised by electrodes intermediate said first pair, means for deriving a control signal from said direct current signal and applying the control signal to said high impedance alternating current source to vary the current applied to said first pair of electrodes in dependence upon the conductivity of the liquor sample, and means for measuring said current applied to the first pair of electrodes to derive a signal dependent upon the conductivity of the liquor sample.

5. A system according to claim 4 in which said means for producing the direct current signal comprises a high input impedance amplifier connected across the second pair of electrodes, the output from said amplifier being fed to a rectifier to produce the direct current signal, and the rectifier being constructed such that the direct current signal is proportional to the peak value of the alternating voltage.

6. A system according to claim 5 in which the output of the rectifier is connected to a low pass filter.

7. A system as claimed in claim 5 or 6 in which said means for deriving and applying the control signal comprises a voltage controlled attenuator coupled to the output of the rectifier.

8. A system according to claim 7 in which the attenuator is connected to an alternating current source to produce an alternating current output which is substantially inversely proportional to said direct current signal and which forms said control signal.

9. A system for monitoring the electrical conductivity of a liquor sample comprising a measuring cell having a tubular body portion, at least three cylindrical metallic members coaxially disposed within the body member, a plurality of cylindrical spacers made of electrically non-conductive material disposed between said electrodes in order to space said electrodes apart, one end of each of said metallic members and one end of each said spacer, terminating in a common flat surface to define a plurality of concentric electrodes in said surface which are mutually separated by annular areas of electrically non-conductive material, said surface being presented in use of the system, to said liquor sample under test, a high impedance alternating current source connected across a first pair of said electrodes, means for producing a direct current signal which is dependent upon the alternating voltage across a second pair of said electrodes comprised by electrodes intermediate said first pair, means for deriving a control signal from said direct current signal and applying the control signal to said high impedance alternating current source to vary the current applied to said first pair of electrodes in dependence upon the conductivity of the liquor sample, and means for measuring said current applied to the first pair of electrodes to derive a signal dependent upon the conductivity of the liquor sample.

10. A system for comparing the electrical conductivities of two liquor samples, comprising a pair of electrode cells, one for presentation to each of the two liquor samples, respectively, each cell having at least four concentric, circular electrodes disposed in or on a substantially flat surface and mutually separated by areas of electrically non-conductive material, said surfaces being presented, in use of the system, to said two liquor samples, respectively, a pair of high impedance alternating current sources respectively connected across a first pair of the electrodes of the cells, means for producing respective direct current signals which are dependent upon the alternating voltages across second pairs of said electrodes comprised by electrodes intermediate said first pairs, means for deriving a control signal from the direct current signal from one of said cells and applying this control signal to both the high impedance alternating current sources to vary the current applied to both said first pairs of electrodes in dependence upon the conductivity of the liquor sample in contact with said one of the cells, and means for comparing the two direct current signals from the second pairs of electrodes to provide a signal which depends upon the conductivities of the two liquor samples.

* * * * *